United States Patent [19]

Sasajima et al.

[11] 3,970,522
[45] July 20, 1976

[54] METHOD FOR THE PRODUCTION OF D-RIBOSE

[75] Inventors: Ken-ichi Sasajima, Hyogo; Muneharu Doi; Teruo Fukuhara, both of Osaka; Akira Yokota, Kyoto; Yoshio Nakao, Osaka; Masahiko Yoneda, Kobe, all of Japan

[73] Assignee: Takeda Chemical Industries, Ltd., Osaka, Japan

[22] Filed: Nov. 25, 1974

[21] Appl. No.: 527,145

[30] Foreign Application Priority Data
Nov. 23, 1973 Japan............................. 48-131955
Mar. 18, 1974 Japan............................. 49-31357

[52] U.S. Cl. ............................. 195/112; 195/28 R; 195/31 R; 195/79; 195/96
[51] Int. Cl.² ......................................... C12D 13/02
[58] Field of Search .................. 195/31 R, 28 R, 96, 195/49, 79, 78, 11, 112

[56] References Cited
UNITED STATES PATENTS
3,607,648   9/1971   Yoneda et al...................... 195/28 R
3,919,046   11/1975   Sasajima et al................... 195/96 X

OTHER PUBLICATIONS

Sasajima et al., Chem. Abstracts, vol. 80, p. 309, 144411j (1974).

Sasajima et al., "Carbohydrate Metabolism–Mutants of a Bacillus Species Part II. —D-Ribose Accumulating by Pentose Phosphate Pathway Mutants," Agr. Biol. Chem., vol. 35, No. 4, pp. 509–517, (1971).

Primary Examiner—A. Louis Monacell
Assistant Examiner—Thomas G. Wiseman
Attorney, Agent, or Firm—Wenderoth, Lind & Ponack

[57] ABSTRACT

D-Ribose is produced by cultivating a strain belonging to the genus Bacillus, which lacks sporulation ability or has high 2-deoxy-D-glucose-oxidizing activity or has both of these two properties and also lacks at least one of transketolase and D-ribulose phosphate 3-epimerase, to cause said strain to elaborate and accumulate a large amount of D-ribose. The thus accumulated D-ribose can be recovered in good yield.

13 Claims, No Drawings

METHOD FOR THE PRODUCTION OF D-RIBOSE

This invention relates to a method for producing D-ribose. By the present invention is provided a method for producing D-ribose, which comprises cultivating a D-ribose-producing microorganism belonging to the genus Bacillus, which lacks sporulation ability or has high 2-deoxy-D-glucose-oxidizing activity or has both of these properties and also lacks at least one of transketolase and D-ribulose phosphate 3-epimerase, in a culture medium containing assimilable carbon and nitrogen sources as well as nutrients necessary for the growth of the strain, thereby causing said strain to elaborate and accumulate D-ribose and, then, recovering the D-ribose thus accumulated from the resultant culture broth.

As a constituent of nucleic acids, D-ribose occurs in all organisms, and ribitol, a reduction product of D-ribose, is present in vitamin $B_2$ and ribitol-teichoic acid, a constitutent of cell walls. Thus, it is a very important substance physiologically. Furthermore, D-ribose and its derivatives have so far attracted a great deal of attention as starting materials for the synthesis of vitamin $B_2$ and the so-called nucleic acid condiments and, accordingly, the development of a commercial process for the production of D-ribose has been much desired.

The conventional methods for producing D-ribose include methods for extracting D-ribose from natural products and synthetic methods using furan, D-glucose, etc. as starting materials. There also are reports on the fermentative production of D-ribose, but the fermentation yield is extremely low. Thus, these processes are not fully satisfactory as commercial processes for the production of D-ribose.

In connection with the methods of producing D-ribose comprising utilization of Bacillus organisms, Sasajima and Yoneda, who are among the present inventors, previously disclosed the method in which a D-ribose-producing microorganism of the genus Bacillus which requires L-tyrosine, L-tryptophan and L-phenylalanine for its growth is cultivated in a culture medium containing L-tyrosine, L-tryptophan and L-phenylalanine, each in an amount of more than about 100 γ/ml. and the method in which transketolase-lacking strains of the genus Bacillus, Shi 5 and Shi 7 or a D-ribulose phosphate 3-epimerase lacking strain of the genus Bacillus, Gluc 34 are used.

The former method is described in the specification of British Pat. No. 1,255,254 and the latter is described in Agricultural and Biological Chemistry Vol. 35, page 509 (1971).

Concerning the strains used in the former method, however, no apparent mention has been made as to degrees of their sporulation frequency, strength of their 2-deoxy-D-glucose-oxidizing activity, transketolase activity and D-ribulose phosphate 3-epimerase (hereinafter this enzyme is referred to as epimerase) activity.

The presence of the ability to sporulate in these strains is obvious at least from the fact that sporulation is one of the salient characters of microorganisms of the genus Bacillus and also from the axiom that, generally, the absence of any special reference to sporulation in a statement as to a microorganism of the genus Bacillus implies that the particular microorganism is able to sporulate [Bergey's Manual of Determinative Bacteriology, 7th ed. 613 (1957)].

Moreover, these known strains are very meager in 2-deoxy-D-glucose-oxidizing activity, as measured by the 2-deoxy-D-glucose-oxidizing activity assay method described hereinafter, said enzymatic activity of these strains being 0.01–0.02 $\mu$ mole per minute per mg. of protein.

As the above-mentioned reports themselves admit, the amount of D-ribose obtained by these methods is as low as about 35.3 mg./ml. at best.

The 2-deoxy-D-glucose-oxidizing activity of these strains, obtained by the assay method, and the highest amount of D-ribose accumulated in the broth described in the above-mentioned reports are listed below.

|  | Microorganism | 2-deoxy-D-glucose-oxidizing activity ($\mu$mole/min./mg. protein) | D-ribose accumulated (mg./ml.) |
|---|---|---|---|
| British Patent Specification No. 1255254 | Bacillus pumilus No.503 | 0.01 | 28.5 |
|  | Bacillus pumilus No.537 | 0.02 | 30.5 |
|  | Bacillus pumilus No.558 | 0.01 | 29.3 |
|  | Bacillus subtilis No.429 | 0.01 | 26.5 |
|  | Bacillus subtilis No.483 | 0.01 | 29.5 |
| Agricultural and Biological Chemistry 35, 509(1971) | Bacillus species Shi 5 | 0.01 | 28.4 |
|  | Bacillus species Shi 7 | 0.02 | 35.3 |
|  | Bacillus species Gluc 34 | 0.01 | 24.8 |

In an attempt to develop a production method for D-ribose through utilization of bacteria of the genus Bacillus that would produce D-ribose in high fermentation yields, the present inventors began intensive research which ultimately resulted in with a novel finding that those mutants of bacteria of the genus Bacillus which were concurrently lacking at least one of transketolase and epimerase and had the lack of sporulation ability and/or high 2-deoxy-D-glucose-oxidizing activity had an unusually high ability to accumulate D-ribose. The additional research that ensued has resulted in the present invention, according to which D-ribose can be produced and accumulated at the rate of as high as about 65–70 mg./ml.

Heretofore, broadly in connection with methods for producing D-ribose by means of microorganisms, there has not been any study directed to the relation of ability to sporulate and the yield of D-ribose. This invention is the outcome of the first study of the kind. In addition to the increased yield of D-ribose which can thus be realized by the working of this invention, the invention has the additional advantage that, though this is a natural outcome of the lack of sporulation, the method does not require the troublesome procedure of removing the spores and makes it very easy to recover the contemplated product.

The lack of sporulation as the term is used in this specification means that, when the total viability of the population and the spore counts are measured by a method described below, which is analogous to that described in Journal of General and Applied Microbiology vol. 16, page 430, last line to 431, line 5 (1970), the spore counts divided by the total viability of the population, that is "sporulation frequency", is not more than $10^{-4}$.

Procedure for Determination of Sporulation Frequency

A loopful of a slant culture of the strain whose sporulation frequency is to be determined is transferred into 5 ml. of a modified Schaeffer's medium [Proceedings of the National Academy of Sciences of the United States, Vol. 54, page 704 (1965)] containing 1.0 % of D-glucose, 0.8 % of Difco nutrient broth, 0.01 % of shikimic acid, 0.025 % of $MgSO_4.7H_2O$, 0.1 % of KCl, $10^{-6}M$ $FeCl_3.6H_2O$, $10^{-3}M$ $CaCl_2.2H_2O$ and $10^{-5}M$ $MNCl_2.4H_2O$, among which $CaCl_2.2H_2O$ and $MnCl_2.4H_2O$ were sterilized separately. The medium was adjusted to pH 7.0 before sterilization. After the three day incubation at 37°C, the culture was divided into two 2.5 ml. portions, one of which was heated at 80°C for 30 min. Both the non-heated culture (total viability) and the heated culture (spore counts) were diluted appropriately and spread on a modified Schaeffer's agar medium which was prepared by adding 2 % of agar to the modified Schaeffer's medium described above. Viable cells were counted after incubation at 37°C for 2 days. The sporulation frequency of the test strain is the value of the spore counts divided by the total viability of the population.

In this specification, the lack of transketolase or epimerase, means that when, by the following method, the discipline of which is described in Journal of Biological Chemistry 223, 1009 (1956), Archives of Biochemistry and Biophysics vol. 74, page 306 (1958) and ditto vol. 74, page 315 (1958), the amount of oxidation of reduced form of nicotinamide adenine dinucleotide (hereinafter referred to as NADH) is measured and the particular enzymatic activity is calculated for the cell extract (A) prepared by the procedure set forth below, the value is not more than 0.01 $\mu$ mole/min./mg. protein.

(I) Procedure for the Preparation of a Cell Extract (A)

A slant culture of a strain whose transketolase activity or epimerase activity is to be determined is inoculated into a culture medium (pH 7.0) containing 2.0 % of sorbitol, 0.1 % of sodium L-glutamate, 0.1 % of $KH_2SO_4$, 0.3 % of $K_2HPO_4$, 0.5 % of $(NH_4)_2SO_4$, 0.1 % of $MgSO_4.7H_2O$, 0.001 % of $FeSO_4.7H_2O$, 0.001 % of $ZnSO_4.7H_2O$, 0.001 % of $MnSO_4.4-6H_2O$, 100–4000 $\mu$g./l. of biotin, 100–3000 $\mu$g./l. of thiamine hydrochloride and 100 $\mu$g./ml. of shikimic acid and the inoculated medium is incubated under shaking at 32°–37°C for 24 hours. The resultant culture broth is centrifuged to harvest the cells which, in turn, are washed twice with 0.01 M tris(hydroxymethyl)aminomethane-HCl buffer solution (pH 7.5) containing 0.001 M of mercaptoethanol and resuspended in the same buffer as above to make a cell suspension whose absorbance at 650 nm is 10. Then, egg-white lysozyme is added to the suspension to give a concentration of 50 $\mu$g./ml. and after the reaction is allowed to take place at 37°C for 30–90 minutes, the system is centrifuged. The resultant supernatant fluid is used as the above-mentioned cell extract (A).

(II)-1 Solutions for Assay of Transketolase Activity

Reaction Solution A: (1.11 ml.)

20 $\mu$ moles of D-ribose-5-phosphate, 0.5 $\mu$ mole of NADH, sufficient D-ribose-5-phosphate ketol-isomerase and epimerase, 0.66 unit of $\alpha$-glycerophosphate dehydrogenase containing sufficient triosephosphate isomerase, 0.43 $\mu$ mole of thiamine pyrophosphate and 40 $\mu$ moles of tris(hydroxymethyl)aminomethane-HCl buffer solution (pH 7.5).

Reaction Solution B: (0.89 ml.)

20 $\mu$ moles of $MgCl_2$, 0.43 $\mu$ mole of thiamine pyrophosphate, 40 $\mu$ moles of tris(hydroxymethyl)aminomethane-HCl buffer solution (pH 7.5), and 10 $\mu$l. of the enzyme solution.

(II)-2 Solutions for Assay of Epimerase Activity

Reaction Solution A (0.9 ml.)

20 $\mu$ moles of D-ribose-5-phosphate, 20 $\mu$ moles of $MgCl_2$, 0.43 $\mu$ mole of thiamine pyrophosphate, sufficient transketolase, and 40 $\mu$ moles of tris(hydroxymethyl)aminomethane-HCl buffer solution (pH 7.5).

Reaction Solution B (1.09 ml.)

0.5 $\mu$ mole of NADH, 0.66 unit of $\alpha$-glycerophosphate dehydrogenase containing sufficient triosephosphate isomerase, sufficient D-ribose-5-phosphate ketol-isomerase and transketolase, and 60 $\mu$ moles of tris(hydroxymethyl)aminomethane-HCl buffer solution (pH 7.5).

(III)-1 Procedure for Assay of Transketolase Activity

Each reaction solution is incubated at 30°C for 10 min. and then the reaction solutions are mixed (the total volume is 2 ml.). The change of absorbance at 340 nm was measured with a Gilford Multiple Sample Absorbance Recorder 2000 (Gilford Instrument Laboratories Inc., U.S.A.) at 30°C.

(III)-2 Procedure for Assay of Epimerase Activity

The reaction solution A is incubated at 30°C for 30 min. and the reaction solution B is incubated at 30°C for 10 min.

The reaction solutions are mixed, then 10 $\mu$l. of the enzyme solution is added to the mixture (the total volume is 2 ml.).

The change of absorbancy at 340 nm was measured in the same method as the case of transketolase.

(IV) Calculation of Enzyme Activity

The enzyme activity ($\mu$ mole/min./mg. protein) in the enzyme solution is expressed by the following formula:

$$-\Delta E_{340/min.} \times \frac{V}{\Sigma \times d \times E \times p}$$

wherein $-\Delta^E 340/min.$ is the velocity of decrease of the net absorbancy of the mixed reaction solution at 340 nm for one minute, V is the total volume of the mixed reaction solution (2 ml.), $\Sigma$ is the molecular extinction coefficient of NADH at 340 nm (6.22 $cm^2/\mu$ mole), d is the light path (1 cm), E is the volume of the enzyme solution (0.01 ml.), and p is the weight of protein in the enzyme solution (mg./ml.).

In this specification, the high 2-deoxy-D-glucose-oxidizing activity means that when, for the cell extract (B) prepared by the method for preparation of cell extract (B) to be described hereinafter, the amount of reduction of nicotinamide adenine dinucleotide ($NAD^+$) is measured by the use of the reaction solution for assay of 2-deoxy-D-glucose-oxidizing activity, which is also to be described hereinafter, and, on the basis of the said amount, the enzymatic activity of said extract is calculated, according to the formula which is described hereinbefore for expression of transketolase or epemerase activity, the value found is not less than 0.05 $\mu$ mole per minute per milligram of protein but not over 1.00 $\mu$ mole per minute per milligram of protein.

(I) Procedure for the Preparation of Cell Extract (B)

A medium composed of 0.5 % of sorbitol, 0.65 % of sodium L-glutamate, 0.1 % of $KH_2PO_4$, 0.3 % of $K_2HPO_4$, 0.1 % of $Na_2SO_4$, 0.01 % of $MgSO_4 \cdot 7H_2O$, 0.004 % of biotin, 0.0003 % of thiamine hydrochloride and 0.01 % of shikimic acid is inoculated with a strain whose 2-deoxy-D-glucose-oxidizing activity is to be determined from a slant culture and incubated at 37°C under shaking for 20 hours. From the broth, the cells are harvested by centrifugation, washed twice with a 0.01M tris(hydroxymethyl)aminomethane-HCl buffer solution (pH 7.5) containing 0.001 M of mercaptoethanol and resuspended in the same buffer as above to make a cell suspension, the absorbance of which is 100 at 650 nm. The suspension is treated by an ultrasonic disintegrater (Insonater, by Kubota Iron Works, Ltd. Japan) at 160 W for 10 minutes, whereby the cells are disrupted. The sediment is removed by centrifugation. The supernatant fraction is the cell extract (B).

(II) Reaction Solution for Assay of
2-Deoxy-D-Glucose-Oxidizing Activity 1.2 ml. of 1 M tris(hydroxymethyl)aminomethane-HCl buffer solution (pH 8.0), 0.2 ml. of 0.1 mM $MnSO_4 \cdot 4-6H_2O$, 0.2 ml. of 20 m M $NAD^+$, 0.2 ml. of 1 M 2-deoxy-D-glucose, and 0.2 ml. of cell extract (B) (reaction temperature 30°C).

In accordance with this invention, there is employed a strain of the genus Bacillus which is concurrently lacking at least one of transketolase and epimerase and has at least one of high 2-deoxy-D-glucose-oxidizing activity and asporogenous property. Such strains can be easily derived from microorganisms belonging to the genus Bacillus such as, *Bacillus, brevis, Bacillus cereus, Bacillus circulans, Bacillus coagulans, Bacillus licheniformis, Bacillus megaterium, Bacillus mesentericus, Bacillus pumilus, Bacillus subtilis*, etc., by means such as, irradiating the parent strains with radiation such as ultraviolet light, X-rays, gamma rays or the like or exposing the parent strains to the action of chemical mutagens such as N-methyl-N'-nitro-N-nitrosoguanidine, nitrogen mustard, dimethylsulfoxide, ethylmethanesulfonate, etc. It is, of course, possible to obtain a strain lacking at least one of transketolase and epimerase in the first place and cause the strain to undergo further mutation to a strain having at least one of asporogenous property and high 2-deoxy-D-glucose-oxidizing activity, or to reverse the procedure to obtain the contemplated mutant. Among examples of the strains employable according to this invention are *Bacillus pumilus* No. 911 (IFO 13566), No. 1027 (IFO 13585) and No. 1083 (IFO 13620) and *Bacillus subtilis* No. 957 (IFO 13565), No. 941 (IFO 13573), No. 1054 (IFO 13586), No. 1067 (IFO 13588) and No. 1097 (IFO 13621) and so on.

The numbers following IFO mean the accession numbers at the Institute for Fermentation, Osaka, Japan.

Referring to the nutrients that are used as the constituents of a medium for the cultivation of microorganisms according to this invention, the carbon sources include, among others, D-glucose, D-fructose, D-mannose, sorbitol, D-mannitol, sucrose, molasses, starch hydrolyzates, starch, acetic acid and ethanol. The nitrogen sources include organic nitrogen sources such as corn steep liquor, cottonseed refuse, yeast extract, dried yeast, fish meal, meat extract, peptone, casamino acid, etc., inorganic nitrogen compounds such as aqueous ammonia, ammonia gas, ammonium sulfate, ammonium nitrate, ammonium chloride, ammonium carbonate, ammonium phosphate, sodium nitrate, etc., and organic nitrogen compounds such as urea, amino acids, etc. Also incorporated in the medium, in addition to said carbon and nitrogen sources, are various metals, vitamins, amino acids and other substances which may be essential to the growth of the particular microorganism, the proportions of which are optional.

The cultivation is conducted aerobically, for example by shaking culture or submerged culture under sparging and stirring. The incubation temperature is usually selected from within the range of 20° to 45°C, depending upon the temperature suited for the particular organism to grow and accumulate D-ribose. The pH of the medium is preferably somewhere between about 5 and about 9.

To maintain the pH within the optimum range throughout the cultivation period, one may incorporate from time to time such a neutralizer as hydrochloric acid, sulfuric acid, aqueous ammonia, ammonia gas, an aqueous solution of sodium hydroxide, calcium carbonate, slaked lime, etc. Ordinarily, a substantial amount of D-ribose accumulates in the medium in about 2 to 5 days.

The D-ribose thus accumulated can be easily recovered, for example, by the following procedure. Namely, the culture broth is first filtered or centrifuged, whereby the cells can be removed with great ease. Then, the filtrate is desalted and decolorized by treatment with activated carbon and ion exchange resin and, then, concentrated.

To the concentrate is added an organic solvent such as ethanol, whereupon D-ribose crystals separate. Whether the above or other method is employed, D-ribose can be easily recovered.

The following examples are further illustrative of this invention, it being understood, however, that the invention is by no means limited thereto.

In the present specification percentages are shown by weight/volume unless otherwise specified.

EXAMPLE 1

A transketolase-lacking, asporogenous mutant No. 911 of *Bacillus pumilus* (IFO 13566), which had been derived from *Bacillus pumilus* IFO 12113 by irradiation of ultraviolet-rays, (transketolase activity: not more than 0.01 $\mu$ mole/min./mg. protein; sporulation frequency: $2 \times 10^{-8}$) was used to inoculate 10 l. of a medium comprising 2.0 % of sorbitol, 2.0 % of corn steep liquor, 0.3 % of dipotassium hydrogenphosphate, 0.1 % of potassium dihydrogen phosphate, 100 $\mu$g./ml. of tyrosine and 100 $\mu$g./ml. of phenylalanine and the inoculated medium was incubated at 36°C for 24 hours. The entire amount of the resultant culture was transferred to 100 l. of a culture medium comprising 15.0 % of D-glucose, 1.0 % of dried yeast, 0.5 % of ammonium sulfate, 2.0 % of calcium carbonate, 50 $\mu$g./ml. of tryptophan, 50 $\mu$g./ml. of tyrosine and 50 $\mu$g./ml. of phenylalanine, in which it was cultivated at 36°C for 60 hours, whereupon D-ribose accumulated at the rate of 64 mg./ml. From this D-ribose fermentation broth, the cells were removed by filtration and the filtrate was concentrated to half the original volume. Then, about one-quarter of its volume of ethanol was added and the precipitate was discarded. The residue is desalted with cation and anion exchange resins and, then, decolorized on a column of activated carbon.

The decolorized solution was concentrated and about 4 times its volume of ethanol was added, whereby 5.0 kg. of crystalline D-ribose was obtained.

EXAMPLE 2

A transketolase-lacking, asporogenous mutant No. 957 of *Bacillus subtilis* (IFO 13565), which had been derived from *Bacillus subtilis* IFO 3026 by treatment with N-methyl-N'-nitro-N-nitrosoguanidine (NTG), (transketolase activity: not more than 0.01 $\mu$ mole/min./mg. protein; sporulation frequency: $8\times10^{-5}$), was cultivated by a procedure similar to that described in Example 1, whereby D-ribose accumulated in the broth at the rate of 62 mg./ml. From this broth, 4.6 kg. of crystalline D-ribose were obtained in the same manner as Example 1.

EXAMPLE 3

An epimerase-lacking, asporogenous mutant No. 941 of *Bacillus subtilis* (IFO 13573), which had been derived from *Bacillus subtilis* IFO 3026 by irradiation of ultraviolet-rays (epimerase activity: not more than 0.01 $\mu$ mole/min./mg. protein; sporulation frequency: $7\times10^{-6}$), was cultivated in the same manner as Example 1, whereby D-ribose accumulated at the rate of 65 mg./ml. From this broth, 4.3 kg. of D-ribose crystals were obtained in the same manner as Example 1.

EXAMPLE 4

Mutant No. 1027 of *Bacillus pumilus* (IFO 13585) lacking transketolase and having high 2-deoxy-D-glucose-oxidizing activity (transketolase activity: not more than 0.01 $\mu$ mole/min./mg. protein; 2-deoxy-D-glucose-oxidizing activity: 0.28 $\mu$ mole/min./mg.-protein) which had been derived from *Bacillus pumilus* IFO 12092 by irradiation of ultraviolet-rays, was cultivated by a procedure similar to that described in Example 1, whereby D-ribose accumulated in the broth at the rate of 63.2 mg./ml. From this broth, 48 kg. of D-ribose crystals were obtained in the same manner as Example 1.

EXAMPLE 5

Mutant No. 1054 of *Bacillus subtilis* (IFO 13586) lacking epimerase and having high 2-deoxy-D-glucose-oxidizing activity (epimerase activity: not more than 0.01 $\mu$ mole/min./mg. protein; 2-deoxy-D-glucose-oxidizing activity: 0.31 $\mu$ mole/min./mg. protein), which had been derived from *Bacillus subtilis* IFO 3026 by treatment with N-methyl-N'-nitro-N-nitrosoguanidine, was cultivated by a procedure similar to that described in Example 1, whereby D-ribose accumulated in the broth at the rate of 65.7 mg./ml. From this broth, 5.1 kg. of D-ribose crystals were obtained in the same manner as Example 1.

EXAMPLE 6

Mutant No. 1067 of *Bacillus subtilis* (IFO 13588) lacking transketolase and haivng high 2-deoxy-D-glucose-oxidizing activity (transketolase activity: not more than 0.01 $\mu$ mole/min./mg. protein: 2-deoxy-D-glucose-oxidizing activity: 0.33 $\mu$ mole/min./mg. protein), which had been derived from *Bacillus subtilis* IFO 3026 by treatment with N-methyl-N'-nitro-N-nitrosoguanidine, was cultivated by a procedure similar to that described in Example 1, whereby D-ribose was accumulated in the broth at the rate of 66.5 mg./ml. From this broth, 5.3 kg. of D-ribose crystals were obtained in the same manner as Example 1.

EXAMPLE 7

A transketolase-lacking, asporogenous, high 2-deoxy-D-glucose-oxidizing activity mutant No. 1083 of *Bacillus pumilus* (IFO 13620) (transketolase activity: not more than 0.01 $\mu$ mole/min./mg. protein; sporulation frequency: $4\times10^{-6}$; 2-deoxy-D-glucose-oxidizing activity: 0.34 $\mu$ mole/min./mg. protein) which had been derived from *Bacillus pumilus* S-1 [this strain was isolated from soil and identified with *Bacillus pumilus* according to the description in Bergey's Manual of Determinative Bacteriology, pages 620–622 (1957)], by irradiation of ultraviolet-rays was cultivated by a procedure similar to that described in Example 1, whereby D-ribose accumulated in the broth at the rate of 72.3 mg./ml. From this broth, 5.6 Kg. of crystalline D-ribose was obtained in the same manner as Example 1.

EXAMPLE 8

A transketolase-lacking, asporogenous, high 2-deoxy-D-glucose-oxidizing activity mutant No. 1097 of *Bacillus subtilis* (IFO 13621) (transketolase activity: not more than 0.01 $\mu$ mole/min./mg. protein; sporulation frequency $3\times10^{-7}$; 2-deoxy-D-glucose-oxidizing activity: 0.29 $\mu$ mole/min./mg. protein) which had been derived from *Bacillus subtilis* IFO 3026 by irradiation of ultraviolet-rays, was cultivated by a procedure similar to that described in Example 1, whereupon D-ribose accumulated in the broth at the rate of 70.5 mg./ml. From this broth, 5.4 Kg. of crystalline D-ribose were obtained in the same manner as Example 1.

All strains used in the foregoing examples have been deposited at American Type Culture Collection, Md., U.S.A. under the accession numbers listed below:

| Example | Strain | Accession No. |
|---|---|---|
| 1 | Bacillus pumilus No.911 | ATCC 31095 |
| 2 | Bacillus subtilis No.957 | ATCC 31096 |
| 3 | Bacillus subtilis No.941 | ATCC 31097 |
| 4 | Bacillus pumilus No.1027 | ATCC 31098 |
| 5 | Bacillus subtilis No.1054 | ATCC 31091 |
| 6 | Bacillus subtilis No.1067 | ATCC 31092 |
| 7 | Bacillus pumilus No.1083 | ATCC 31093 |
| 8 | Bacillus subtilis No.1097 | ATCC 31094 |

What we claim is:

1. A method of producing D-ribose, which comprises cultivating a microorganism belonging to the genus Bacillus in a culture medium containing assimilable carbon and nitrogen sources and factors necessary for growth of the microorganism, causing the microorganism to elaborate and accumulate D-ribose, and recovering the D-ribose thus accumulated from the resultant culture broth, said microogranism having at least one property selected from the group consisting of (1) a sporulation frequency not more than $10^{-4}$ and (2) a 2-deoxy-D-glucose-oxidizing activity within the range from 0.05 to 1.00 $\mu$ mole/min./mg. protein, and said microorganism also having at least one property selected from the group consisting of (3) a transketolase activity of not more than 0.01 $\mu$ mole/min./mg. protein and (4) a D-ribulose phosphate 3-epimerase activity of not more than 0.01 μ mole/min./mg. protein.

2. A method according to claim 1, wherein the factors which are necessary for growth of the microorganism are various metals, vitamins and amino acids.

3. A method according to claim 1, wherein the microorganism is cultivated in the culture medium having a pH of from 5 to 9 at a temperature of from 20° to 45°C under aerobic condition.

4. A method according to claim 1, wherein the microorganism is a mutant of *Bacillus pumilus*.

5. A method according to claim 4, wherein the microorganism is *Bacillus pumilus* No. 911.

6. A method according to claim 4, wherein the microorganism is *Bacillus pumilus* No. 1027.

7. A method according to claim 4, wherein the microorganism is *Bacillus pumilus* No. 1083.

8. A method according to claim 1, wherein the microorganism is a mutant of *Bacillus subtilis*.

9. A method according to claim 8, wherein the microorganism is *Bacillus subtilis* No. 957.

10. A method according to claim 8, wherein the microorganism is *Bacillus subtilis* No. 941.

11. A method according to claim 8, wherein the microorganism is *Bacillus subtilis* No. 1054.

12. A method according to claim 8, wherein the microorganism is *Bacillus subtilis* No. 1067.

13. A method according to claim 8, wherein the microorganism is *Bacillus subtilis* No. 1097.

* * * * *